US012797216B2

(12) United States Patent
Ueda et al.

(10) Patent No.: US 12,797,216 B2
(45) Date of Patent: Nov. 17, 2026

(54) BALLOON CATHETER

(71) Applicant: Toray Industries, Inc., Tokyo (JP)

(72) Inventors: Shodai Ueda, Otsu (JP); Takahiro Yagi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 374 days.

(21) Appl. No.: 18/686,795

(22) PCT Filed: Aug. 31, 2022

(86) PCT No.: PCT/JP2022/032770
§ 371 (c)(1),
(2) Date: Feb. 26, 2024

(87) PCT Pub. No.: WO2023/033045
PCT Pub. Date: Mar. 9, 2023

(65) Prior Publication Data

US 2024/0350288 A1 Oct. 24, 2024

(30) Foreign Application Priority Data

Aug. 31, 2021 (JP) ................................ 2021-140659

(51) Int. Cl.
*A61F 2/958* (2013.01)
*A61M 25/00* (2006.01)
*A61M 25/10* (2013.01)

(52) U.S. Cl.
CPC ........... *A61F 2/958* (2013.01); *A61M 25/005* (2013.01); *A61M 25/104* (2013.01)

(58) Field of Classification Search
CPC .............. A61M 25/005; A61M 25/104; A61M 25/10; A61M 2025/1075; A61M 2210/12;
(Continued)

(56) References Cited

U.S. PATENT DOCUMENTS 10,179,047 B2 1/2019 Lee et al.
11,266,426 B2 3/2022 Johnson
(Continued)

FOREIGN PATENT DOCUMENTS

JP 2016-52447 A 4/2016
JP 2019-146600 A * 9/2019 ......... A61B 17/3207
(Continued)

OTHER PUBLICATIONS

Extended European Search Report and Opinion dated Jul. 8, 2025, from counterpart European Patent Application No. 22864627.9.
(Continued)

*Primary Examiner* — James D Ponton
*Assistant Examiner* — John A Doubrava
(74) *Attorney, Agent, or Firm* — DLA Piper LLP (US)

(57) ABSTRACT

A balloon catheter includes: an outer cylinder shaft having flexibility; an inner cylinder shaft having flexibility and inserted into the outer cylinder shaft; a balloon fixed to the outer cylinder shaft, that inflates or deflates in the transverse direction due to the pressure of an internal fluid supplied through the space within the outer cylinder shaft; and a securing member provided on the outer peripheral side of the balloon, whose diameter expands or contracts in the transverse direction independently of the balloon, due to the mutual movement of the outer cylinder shaft and the inner cylinder shaft in the longitudinal direction thereof; wherein the distal end portion of the inner cylinder shaft and the distal end portion of the securing member are fixed to each other, and the distal end portion of the outer cylinder shaft and the rear end portion of the securing member are fixed to each other.

19 Claims, 3 Drawing Sheets

(58) Field of Classification Search
CPC ........... A61B 2017/00783; A61B 2017/22098; A61B 2017/22001; A61B 2017/22051; A61B 17/22; A61F 2/958
See application file for complete search history.

(56) References Cited

U.S. PATENT DOCUMENTS

| | | | |
|---|---|---|---|
| 2010/0094213 | A1 | 4/2010 | Horn et al. |
| 2015/0011933 | A1 | 1/2015 | Matsuura |
| 2021/0045872 | A1 | 2/2021 | Kheradvar et al. |

FOREIGN PATENT DOCUMENTS

| | | | |
|---|---|---|---|
| JP | 2020-62399 | A | 4/2020 |
| JP | 2021-13743 | A | 2/2021 |
| WO | 2012070570 | A1 | 5/2012 |

OTHER PUBLICATIONS

International Search Report dated Oct. 25, 2022, of counterpart International Application No. PCT/JP2022/032770 along with an English translation.
Saxon, J. T. et al., "Bioprosthetic Valve Fracture During Valve-in-valve TAVR: Bench to Bedside," *Interventional Cardiology Review*, 2018, vol. 13, No. 1, pp. 20-26.

* cited by examiner

BALLOON CATHETER

TECHNICAL FIELD

This disclosure relates to a balloon catheter used in the medical field.

BACKGROUND

A medical balloon catheter generally includes a shaft and a balloon formed at the distal end thereof, and performs a minimally invasive treatment by inflating the balloon. Specific examples of therapeutic applications include treatment methods such as cardiac arrhythmia treatment, embolic material removal, angioplasty and balloon aortic valvuloplasty.

In angioplasty or balloon aortic valvuloplasty, among the methods described above, a balloon catheter can be used for expanding the interior of a body lumen with a stenosis using the balloon of the balloon catheter itself, or for delivering an expandable endoprosthesis such as a stent into a body lumen, and then inflating the balloon to deploy the endoprosthesis.

Further, in performing a treatment to place a new prosthetic valve transcatheterly due to the deterioration of a surgically implanted prosthetic valve, there are situations where the valve area decreases. Therefore, a treatment to fracture the frame of the surgically implanted prosthetic valve can be performed, by inflating the balloon of a balloon catheter to increase the valve area.

The inflation pressure required in a treatment using a balloon catheter varies depending on the treatment method. For example, an inflation pressure of 2 to 3 atm or more is required in treating a stenosis of the aortic valve (aortic valve stenosis), and an inflation pressure of 7 atm or more is required for the balloon to expand and place a stent. Further, an inflation pressure of 15 atm or more is required for fracturing the frame of a surgically implanted prosthetic valve.

In the technique to expand the site of lesion or an organ such as a blood vessel by a balloon catheter, a balloon catheter has been reported, to achieve both the flexibility that enables to conform to the bending of a biological lumen and the strength sufficient for the expanding. That balloon catheter includes a balloon having two layers composed of an inner layer and an outer layer, wherein a reinforcing member in the form of a cylindrical mesh is provided between the inner layer and the outer layer, and wherein the reinforcing member is fixed only at the ends of the inner layer and the outer layer, and the intermediate portion of the reinforcing member is not directly fixed (JP 2016-052447 A).

In the technique to deliver and deploy an expandable endoprosthesis such as a prosthetic valve or a stent to a target site within a body lumen, a balloon catheter has been reported which includes an adjustment device for adjusting the position of the balloon relative to a pressure-bonding type prosthetic valve, to allow a physician to accurately control the positioning of the prosthetic valve in a desired implant position (JP 2020-062399 A).

Further, there has been reported a procedure to fracture a prosthetic valve, by using a balloon in which high strength fibers in the form of a helix is provided in the interior thereof, to achieve an improved pressure resistance (John T Saxon et al., "Bioprosthetic Valve Fracture During Valve-in-valve TAVR: Bench to Bedside", Interventional Cardiology Review, vol. 13, No. 1, Issued on January 2018, p. 20 to 26).

Still further, to remove blood clots, thrombi, occlusions or obstacles obstructing the blood flow in arteries, there is a technique to allow a stentriever deployed by self-expansion to engage with and to remove internal blood clots. An intravascular device has been reported, which is placed by further expanding a self-expandable stentriever by a semi-compliant balloon, after removing blood clots, and then separating the device from the shaft (JP 2021-013743 A).

The catheter disclosed in JP 2016-052447 A includes a member (such as high strength fibers having a tensile breaking strength of 2 GPa or more and elastic modulus of 50 GPa or more) in the form of a cylindrical mesh, that constitutes an intermediate layer between the inner layer and the outer layer of the balloon, to improve the pressure resistance. However, when it is intended to inflate the balloon at a desired position, there is a problem that the balloon is swept away by the blood flow to cause a shift in the position thereof upon inflating the balloon at the desired position since the inner layer, the intermediate layer and the outer layer of the balloon are integrated. Further, since the position of the balloon shifts upon inflation, it is necessary to inflate the balloon multiple times for the positioning of the balloon, which causes the blood flow to be blocked every time.

In the catheter disclosed in JP 2020-062399 A, as well, there are examples where the balloon may slip due to the blood flow to cause a shift in the position or may deviate from a desired position, upon inflating the balloon at the desired position. When such a shift in the position of the balloon or the like occurs, it is necessary to deflate the balloon again and to perform the same operation, resulting in a longer surgery time.

In the catheter disclosed in John T Saxon et al., "Bioprosthetic Valve Fracture During Valve-in-valve TAVR: Bench to Bedside", Interventional Cardiology Review, vol. 13, No. 1, Issued on January 2018, p. 20 to 26, as well, there is the problem that the balloon is swept away by the blood flow to cause a shift in the position thereof upon inflating the balloon at the desired position. Further, since the balloon needs to be inflated multiple times because the balloon shifts from the desired position upon inflation, there is a problem that the balloon may be mistakenly inflated at the prosthetic valve cusp or at the left ventricular outflow tract, possibly causing prosthetic valve dysfunction, atrioventricular block or the like.

In the intravascular device disclosed in JP 2021-013743 A, there is a problem that it is difficult to use the device in a technique that requires a high pressure since the device has a structure in which the stentriever can be separated from the shaft. In addition, it is necessary to use a member such as a microcatheter in combination to deliver the stentriever since the stentriever is self-expandable.

It could therefore be helpful to provide a balloon catheter in which the balloon can be reliably secured to a desired position on its own, without blocking the blood flow.

SUMMARY

We thus provide (1) to (7):

(1) A balloon catheter including:

an outer cylinder shaft having flexibility;

an inner cylinder shaft having flexibility and inserted into the outer cylinder shaft;

a balloon which is fixed to the outer cylinder shaft, and which inflates or deflates in the transverse direction due to the pressure of an internal fluid supplied through the space within the outer cylinder shaft; and a securing member which is provided on the outer peripheral side of the balloon, whose diameter expands or contracts in the transverse direction independently of the balloon, due to the mutual movement of the outer cylinder shaft and the inner cylinder shaft in the longitudinal direction thereof;

wherein the distal end portion of the inner cylinder shaft and the distal end portion of the securing member are fixed to each other, and the distal end portion of the outer cylinder shaft and the rear end portion of the securing member are fixed to each other; and the securing member has an opening(s) through which an external fluid can pass when the diameter of the securing member is expanded.

(2) The balloon catheter according to (1), wherein the securing member is composed of a wire(s), and the wire(s) has/have any one of a braided form, a woven form, a helical form and a linear form.

(3) The balloon catheter according to (1) or (2), wherein the wire has a Young's modulus of 60 to 500 GPa, and a tensile strength of 500 MPa or more.

(4) The balloon catheter according to any one of (1) to (3), wherein the inner cylinder shaft includes:

a large diameter portion provided at the distal end of the inner cylinder shaft; and a small diameter portion provided at the proximal end of the inner cylinder shaft, and having an inner diameter smaller than that of the large diameter portion; and the balloon is fixed to the small diameter portion of the inner cylinder shaft; and the securing member is directly fixed to the large diameter portion of the inner cylinder shaft.

(5) The balloon catheter according to any one of (1) to (4), wherein the wire has a cross-sectional area of 0.0019 $mm^2$ or more;

the balloon is composed of one or more layers including a layer of an elastic material; and the balloon catheter is used for the treatment of aortic valve stenosis.

(6) The balloon catheter according to any one of (1) to (4), wherein the wire has a cross-sectional area of 0.0038 $mm^2$ or more;

the balloon is composed of two or more layers including a layer of an elastic material and a braided layer of resin fibers; and the balloon catheter is used for inflating a stent.

(7) The balloon catheter according to any one of (1) to (4), wherein the wire has a cross-sectional area of 0.0063 $mm^2$ or more;

the balloon is composed of three or more layers including a layer of an elastic material and a braided layer of resin fibers; and the balloon catheter is used for fracturing prosthetic valve.

A securing member having an opening(s) is provided on the exterior of the balloon to not block the flow of an external fluid such as blood flow, and the securing member and the balloon can be independently inflated/deflated. Therefore, it is possible to perform a treatment by inflating the balloon, after securing the balloon in a lumen by expanding the diameter of the securing member alone due to the movement of the inner cylinder shaft in the long axis direction thereof, without blocking the external fluid, making it possible to reduce the shift in the position of the balloon while reducing the impact of blocking the blood flow. Further, when the securing member is made of a hard material, it is possible to perform a wide range of techniques, ranging from a technique that requires a high pressure resistance such as fracturing prosthetic valve, which has conventionally been difficult, to aortic valve inflation which can be performed even with a low pressure resistance.

REFERENCE SIGNS LIST

Figure 1:
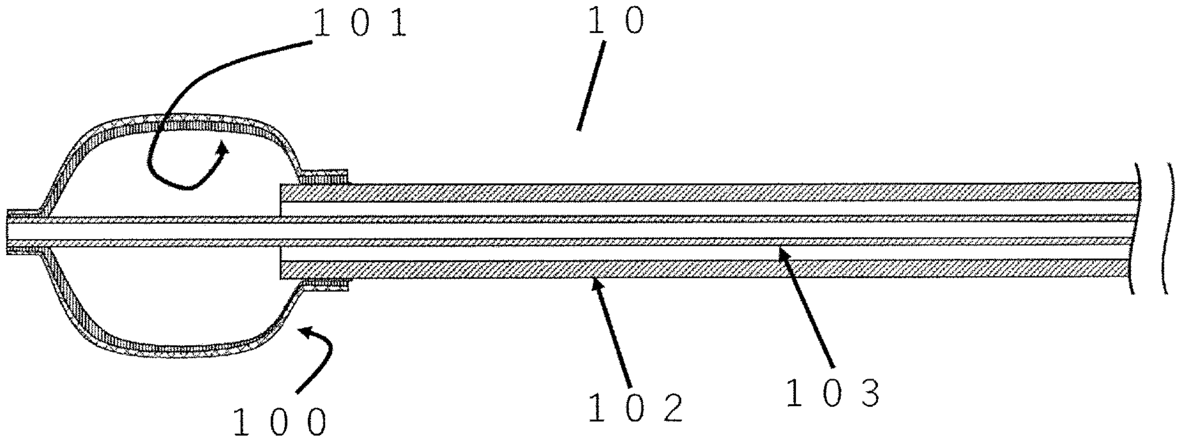
FIG. 1 is a cross-sectional view of a balloon catheter according to a first example, when the diameter of the securing member is expanded and the balloon is inflated.

10 balloon catheter
100 securing member
101 balloon
102 outer cylinder shaft
103 inner cylinder shaft
104 distal end of outer cylinder shaft
105 distal end of inner cylinder shaft
106 braided layer
107 elastic material
108 distal end member
109 large diameter portion of inner cylinder shaft

DETAILED DESCRIPTION

Our balloon catheter is characterized in that it includes:

an outer cylinder shaft having flexibility;

an inner cylinder shaft having flexibility and inserted into the outer cylinder shaft;

a balloon fixed to the outer cylinder shaft, that inflates or deflates in the transverse direction due to the pressure of an internal fluid supplied through the space within the outer cylinder shaft; and a securing member provided on the outer peripheral side of the balloon, whose diameter expands or contracts in the transverse direction independently of the balloon, due to the mutual movement of the outer cylinder shaft and the inner cylinder shaft in the longitudinal direction thereof;

wherein the distal end portion of the inner cylinder shaft and the distal end portion of the securing member are fixed to each other, and the distal end portion of the outer cylinder shaft and the rear end portion of the securing member are fixed to each other; and wherein the securing member has an opening(s) through which an external fluid can pass when the diameter of the securing member is expanded.

Our catheters will be described in detail, with reference to examples.

The term "distal end" refers to the end in the longitudinal direction of a member of a balloon catheter, when the balloon catheter is recognized by an operator, and the term "proximal end" refers to the hand-end side in the longitudinal direction of a member of the balloon catheter, when the balloon catheter is recognized by the operator. The term "to fix" means that two members are fixed to each other, and the members may be fixed via another member(s) unless otherwise specified.

The term "internal fluid" refers to a fluid that flows inside the balloon, and may be, for example, a liquid such as water or saline, or a gas such as nitrogen gas. The term "external fluid" refers to a fluid that flows outside the balloon, and may be, for example, blood or the like that flows outside the balloon, when the balloon catheter is inserted into a blood vessel during the balloon catheter procedure. The term "inflation pressure" refers to the internal pressure generated in the lumen of the balloon, when the internal fluid is injected into the balloon. The term "non-elastic material" refers to a material having a low elasticity, namely, a material having an elastic modulus (Young's modulus) (test method: ISO 6892-1) at normal temperature of about 10 GPa or more.

FIG. 1 is a cross-sectional view of a balloon catheter 10 according to the first example, when the diameter of the securing member is expanded and the balloon is inflated. The balloon catheter 10 shown in FIG. 1 includes a securing member 100, a balloon 101, an outer cylinder shaft 102 and an inner cylinder shaft 103.

Securing Member

Figure 2:
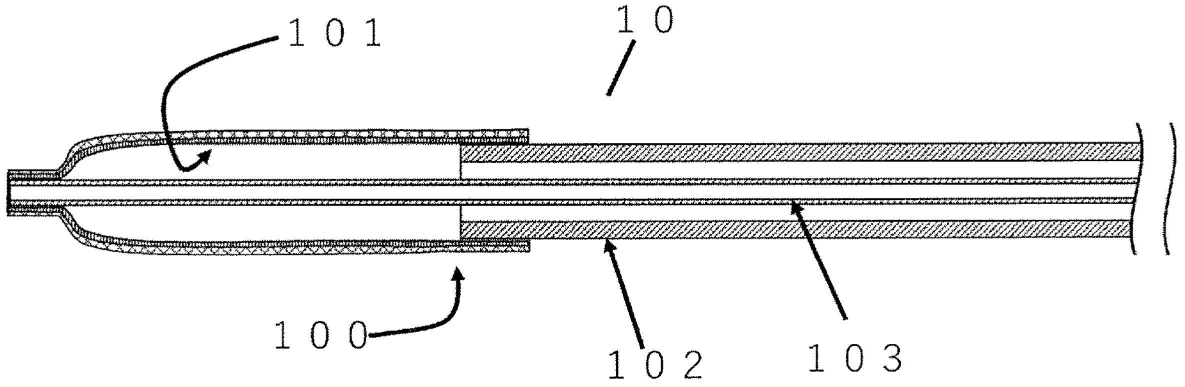
FIG. 2 is a cross-sectional view of a balloon catheter according to the first example, when the diameter of the securing member is contracted and the balloon is deflated.
Figure 3:
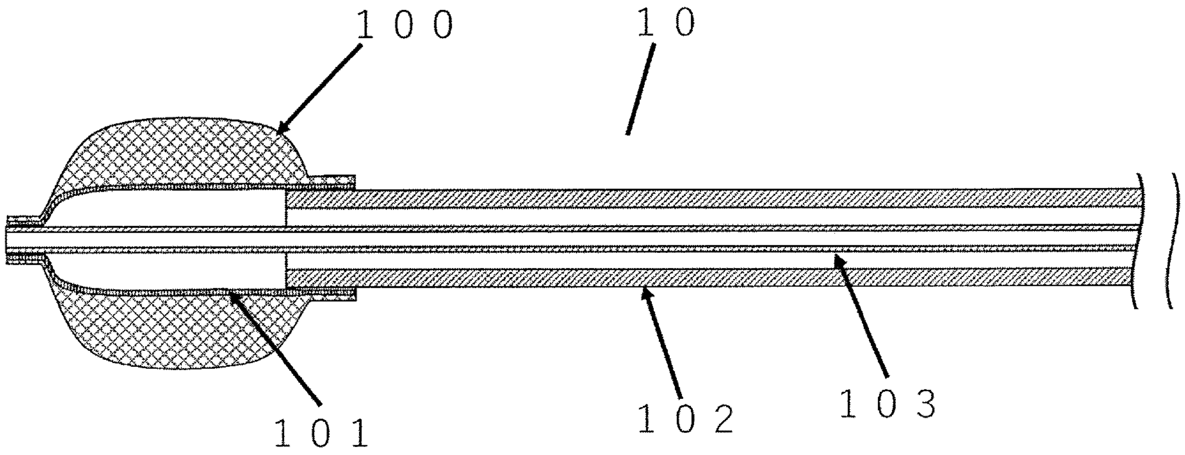
FIG. 3 is a cross-sectional view of a balloon catheter according to the first example, when the diameter of the securing member is expanded and the balloon is deflated.
Figures 4A, 4B, 4C, 4D:
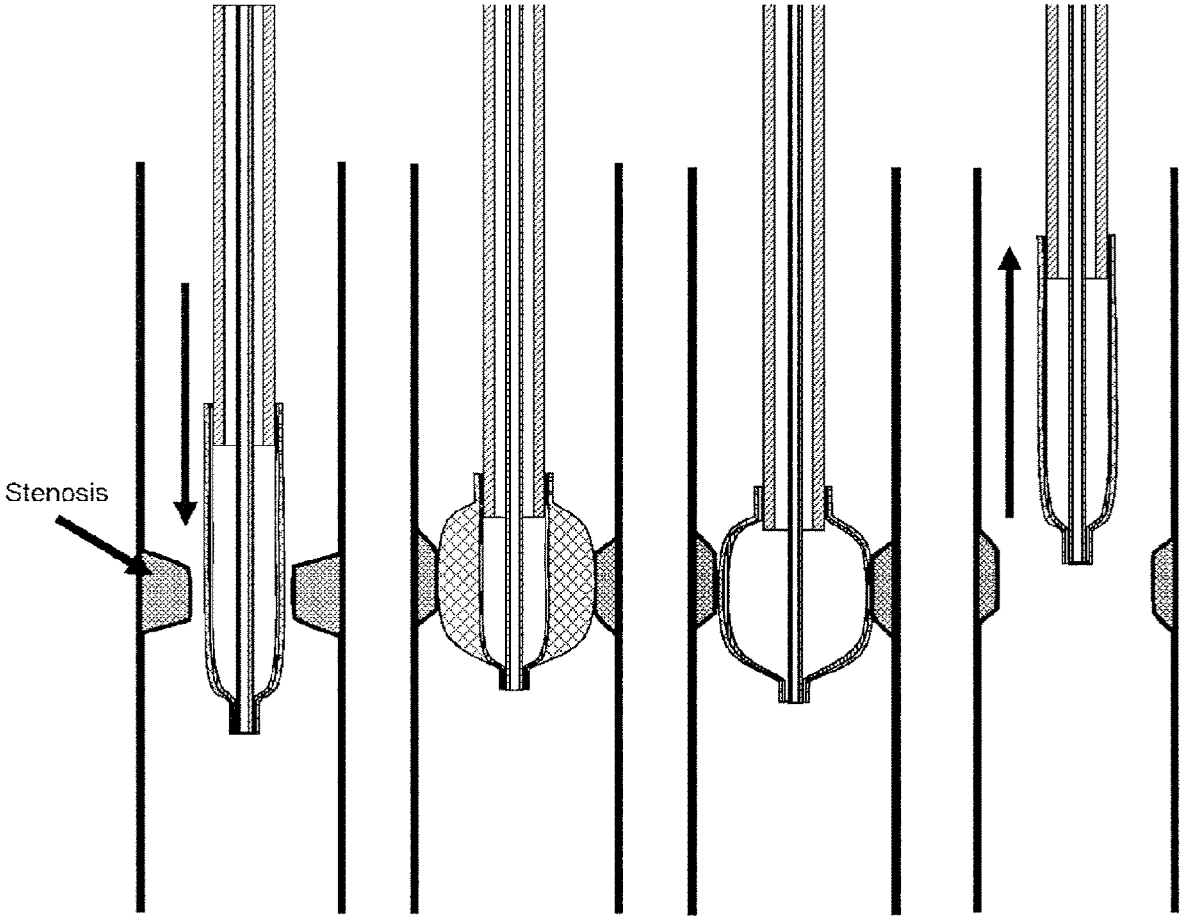
FIGS. 4A to 4D are diagrams showing one example of the treatment method using the first example.

In the securing member 100 in the balloon catheter 10, the distal end portion of the inner cylinder shaft 103 to be described later and the distal end portion of the securing member 100 are fixed to each other, and the distal end portion of the outer cylinder shaft 102 and the rear end portion of the securing member 100 are fixed to each other. Further, the securing member 100 is provided on the outer peripheral side of the balloon 101. Therefore, the structure of the balloon catheter 10 changes, from the state in the cross-sectional view as shown in FIG. 2 in which the diameter of the securing member 100 is contracted and the balloon 101 is deflated due to the mutual movement of the outer cylinder shaft 102 and the inner cylinder shaft 103 in the longitudinal direction thereof, to the state in the cross-sectional view as shown in FIG. 3 in which the diameter of the securing member 100 is expanded and the balloon 101 is deflated, in the order mentioned. In this manner, the diameter of the securing member 100 can be expanded or contracted in the transverse direction independently of the balloon 101, without using the internal fluid. That is, the balloon catheter 10 itself can be secured in a body cavity, by merely moving the inner cylinder shaft 103 at a desired position in the body cavity. For example, the treatment of a stenosis formed in a body cavity using the balloon catheter 10 can be performed by the procedures of the treatment method using the balloon catheter 10 according to the first example shown in FIGS. 4A to 4D. Further, since the securing member 100 has openings through which an external fluid can pass when the diameter of the securing member is expanded, the balloon catheter 10 itself can be secured in a body cavity without blocking the external fluid flowing inside the body cavity.

The securing member 100 is not particularly limited as long as it has a high rigidity and has openings for preventing the external fluid to be blocked. However, the securing member 100 is preferably composed of a wire(s). Specifically, it is preferred that the wire(s) have any one of the following structures: a braided form formed by braiding wires such as resin fibers or metal wires having a linear structure, by tying or intertwining the wires with one another to braid alternately (to cross alternately); a woven form formed by weaving materials such as fibers and metal wires having a linear structure; a helical form formed by winding a single or a plurality of a fiber material(s) in the form of a helix; and a linear form formed by arranging a single or a plurality of fiber material(s) in parallel, in the axial direction of the balloon 101. The wire(s) may have a combined structure of any of these forms.

The braided form or the woven form can be obtained, for example, by braiding, knitting or weaving a plurality of wires made of a non-elastic material. The term "to braid" broadly refers to combining wires with one another to maintain a form, and the term "to knit" refers to a process of forming a fabric-like structure, by tying or intertwining the wires with one another to braid alternately (to cross alternately). The term "to weave" refers to a process of forming a fabric-like structure (a woven fabric structure), by crossing the wires constituting warps and the wires constituting wefts under a certain rule. The opening(s) for preventing the external fluid to be blocked preferably has a size of 0.002 $mm^2$ or more, for example, when the external fluid is blood.

The material of the securing member 100 is not particularly limited. However, the material preferably has a Young's modulus (test method: ISO 6892-1) of 60 GPa to 500 GPa and a tensile strength of 500 MPa or more, and more preferably has a Young's modulus of 100 GPa to 500 GPa and a tensile strength of 500 MPa or more. Further, the securing member 100 is preferably composed of a wire(s) each having a cross-sectional area of 0.0019 $mm^2$ or more and 0.0063 $mm^2$ or less, as a property thereof. In addition, the securing member 100 is preferably made of an X-ray opaque material. For example, it is possible to use carbon or a metal which is medically approved. Examples of the metal include: simple metals such as aluminum, titanium, vanadium, chromium, manganese, iron, cobalt, nickel, copper, niobium, molybdenum, rhodium, palladium, tantalum, tungsten, rhenium, platinum and gold; and alloys containing two or more kinds of metals such as stainless steel. It is preferred to use stainless steel from the viewpoints of workability and economic efficiency. It is preferred to use tungsten or a cobalt-chromium alloy (such as cobalt-chromium-molybdenum) from the viewpoint of Young's modulus. It is preferred to use nickel-titanium from the viewpoint of shape memory properties.

The securing member 100 is not particularly limited as long as the inflation pressure required for the treatment method is achieved. However, for example, the securing member 100 is preferably composed of a wire(s) each having a cross-sectional area of 0.0019 $mm^2$ or more, when used in an application for aortic valve stenosis treatment, which requires an inflation pressure of 2 to 3 atm or more. When used in an application for stent placement, which requires an inflation pressure of 7 atm or more, the securing member 100 is preferably composed of a wire(s) each having a cross-sectional area of 0.0038 $mm^2$ or more. When used in an application for fracturing prosthetic valve, which requires an inflation pressure of 15 atm or more, the securing member 100 is preferably composed of a wire(s) each having a cross-sectional area of 0.0063 $mm^2$ or more.

The cross-sectional shape of the wire(s) constituting the securing member 100 is not particularly limited. However, the cross-sectional shape is preferably circular from the viewpoint of workability, and preferably rectangular from the viewpoints of bendability and the friction of the securing member.

Balloon

Figure 5:
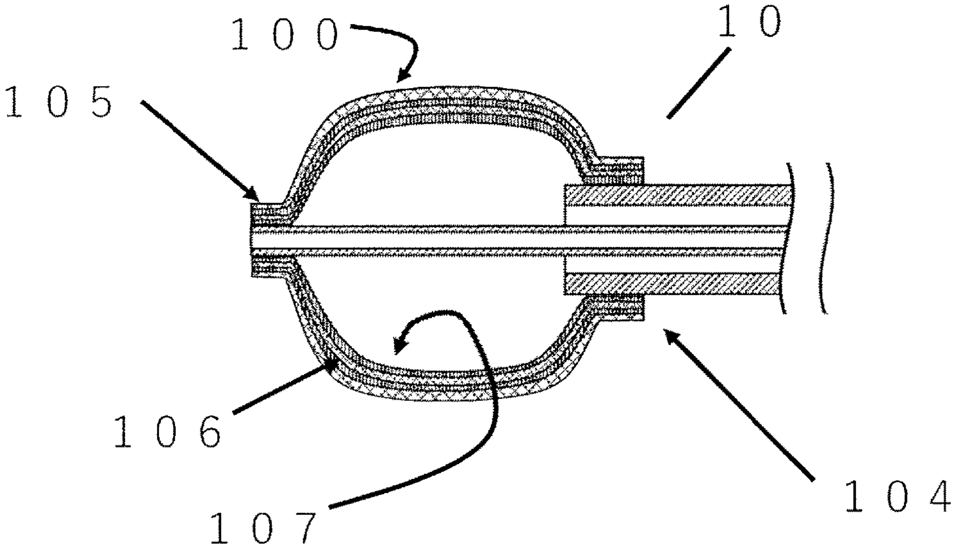
FIG. 5 is a cross-sectional view of a balloon catheter according to a second example, showing the vicinity of the balloon.

The balloon 101 has a structure capable of inflating or deflating in the transverse direction due to the pressure of an internal fluid supplied through the space within the outer cylinder shaft 102 to be described later. The balloon 101 preferably has a structure composed of one layer or a multilayer of two or more layers, as in the cross-sectional view of the balloon catheter of the first example shown in FIG. 1, or as in the cross-sectional view of the balloon catheter of the second example shown in FIG. 5.

When the balloon 101 has a one-layer structure, the balloon preferably consists of a layer of an elastic material 107; when the balloon 101 has a two-layer structure, the inner layer forming the inner surface of the balloon is preferably composed of the layer of the elastic material 107; and when the balloon 101 has a multilayer structure of three or more layers, the surface layer forming the outer surface of the balloon and the inner layer forming the inner surface of the balloon are each preferably composed of the layer of the elastic material 107. The elastic material 107 is not particularly limited, and any common rubber elastic material can be used. For example, the rubber elastic material is preferably one having a JIS-A hardness of 15 to 80. Specific examples of the rubber elastic material include natural rubber (latex), silicone elastomers, thermoplastic elastomers, isobutylene and polybutadiene rubbers, polytetrafluoroethylene, fluorosilicone rubbers, chlorinated polyethylene elastomers, ethylene vinyl acetate, hexafluoropropylene-vinylidene fluoride-tetrafluoroethylene copolymers (for example, FLUOREL (registered trademark) and VITON (registered trademark), both of which are trade names), butyl rubbers, synthetic polyisoprene rubbers, styrene-butadiene rubbers, tetrafluoroethylene-propylene copolymers, thermoplastic co-polyesters, and polyurethanes. Different materials may be selected for different portions of the wall surfaces of the balloon or for different layers of the balloon. Further, two or more kinds of materials may be mixed to adjust the elastic modulus depending on application to be used. It is preferred to use natural rubber (latex) from the viewpoints of workability and economic efficiency, and it is preferred to use a polyurethane from the viewpoints of pressure resistance and economic efficiency.

The term “natural rubber” refers to naturally-occurring rubber, and is usually obtained as natural rubber latex, which is an emulsion in which natural rubber particles are dispersed in a medium such as water.

The balloon 101 may include a braided layer 106 formed by resin fibers, as the surface layer when the balloon 101 has two layers, and as the intermediate layer within the balloon 101 when the balloon 101 has three or more layers, as long as the desired effects are not impaired. The material of the resin fibers is not particularly limited, and any material commonly used for resin fibers can be used. Examples thereof include: polyurethanes, polyolefins such as polyethylene and polypropylene; polyesters such as polyethylene terephthalate, polybutylene terephthalate and polyethylene-2,6-naphthalate; polyamides such as Nylon 6 and Nylon 12; polyvinyl chloride; ethylene vinyl acetate copolymers and saponified products thereof; polystyrene; polycarbonate; polysulfone; polyphenylene oxide; polyphenylene sulfide; aromatic polyamides; polyimides; polyamideimides; cellulose; cellulose acetate; polyvinylidene chloride; polyacrylonitrile; and polyvinyl alcohol; and copolymers thereof. Particularly, a polyester or a polyurethane is preferably used, from the viewpoints of biocompatibility, elastic modulus and the like.

The cross-sectional shape of the resin fibers is not particularly limited, and any of various cross-sectional shapes can be selected as appropriate depending on the application or the required properties. Specifically, the resin fibers may have a perfectly circular cross section or a non-perfectly circular cross section. The non-perfectly circular cross section may specifically be, for example, a multilobed shape, a polygonal shape, a flat shape or an oval shape, the shape of the letter C, the letter H, the letter S, the letter T, the letter W, the letter X, the letter Y, the Chinese character of “rice field” or of well-curbs, a hollow shape or the like, but not limited thereto. It is also possible to use a plurality of kinds of cross-sectional shapes.

When the resin fibers are used in the form of composite false-twisted yarns, the weight ratio of the resin fibers as the core yarns and the resin fibers as the sheath yarns is not particularly limited. For example, in using composite false-twisted yarns of urethane fibers and polyester fibers, and when the weight of the urethane fibers is within 30 to 70% by weight with respect to 100% by weight of the total weight of the yarns, an effect such as an improvement in wear resistance can be expected, because a sufficient stretchability can be obtained and the polyester fibers as the sheath yarns can sufficiently cover the periphery of the core yarns. The degree of interlacing of the composite false-twisted yarns is preferably 50 to 150, but not particularly limited thereto. When the degree of interlacing is 50 or more, the separation of the core yarns from the sheath yarns is reduced. When the degree of interlacing is 150 or less, a decrease in stretch recovery rate does not occur, which is preferred.

Further, the braided layer 106 can be formed by any method as long as it allows for giving elasticity and pressure resistance to the resulting braided layer, and the method may be either warp knitting, weft knitting or plain stich. The braided layer 106 is preferably formed by weft knitting.

The braided layer 106 and the elastic material 107 can be joined, for example, by a method such as pasting using an adhesive, thermocompression bonding, kneading, extrusion molding, resin impregnation or coating, but not particularly limited thereto. For example, the braided layer 106 formed by knitting false twisted yarns composed of a polyurethane and a polyester in the form of a cylinder may be adhered to natural rubber, using a rubber cement, to obtain the balloon.

The elastic material 107 may contain 30% by mass or less of any of various additives with respect to 100% by mass of the elastic material 107, as long as the desired effects are not impaired. An X-ray contrast medium, a colorant, an antioxidant, a thermal stabilizer, a lubricant and/or the like can be used as the above-described various additive(s). The lower limit of the content of the additive(s) is not particularly limited, and there is no problem if the content is 0% by mass with respect to 100% by mass of the elastic material 107. Further, the elastic material 107 may contain 20% by mass or less of inorganic or organic particles with respect to 100% by mass of the elastic material 107, to the extent that the desired performance is not impaired. Examples of the inorganic or organic particles include: particles of calcium carbonate, titanium oxide, silicon oxide, calcium fluoride, lithium fluoride, alumina, barium sulfate, zirconia and calcium phosphate; crosslinked polystyrene-based particles; and metal nanoparticles. The lower limit of the content of the inorganic or organic particles is not particularly limited, and there is no problem if the content is 0% by mass with respect to 100% by mass of the elastic material 107.

The balloon 101 is not particularly limited as long as the inflation pressure required for the treatment method is achieved. However, for example, a balloon composed of one or more layers including the layer of the elastic material 107 is preferred, when used in an application for aortic valve stenosis treatment, which requires an inflation pressure of 2 to 3 atm or more. When used in an application for stent placement, which requires an inflation pressure of 7 atm or more, a balloon composed of two or more layers including the layer of the elastic material 107 as the inner layer, and the braided layer 106 as the surface layer is preferred. When used in an application for fracturing prosthetic valve, which requires an inflation pressure of 15 atm or more, a balloon composed of three or more layers including the layer of the elastic material 107 as the surface layer, the braided layer 106 of resin fibers as the intermediate layer and the layer of the elastic material 107 as the inner layer is preferred.

Outer Cylinder Shaft

The inner cylinder shaft 103 is inserted into the interior of the lumen of the outer cylinder shaft 102, a guide wire is passed through the interior of the inner cylinder shaft 103, and the inner cylinder shaft 103 and the outer cylinder shaft 102 are delivered into the body along the guide wire.

Any tube-shaped member having flexibility can be used as the outer cylinder shaft 102. For example, the outer cylinder shaft 102 is formed from a one-layer tube or a multilayer tube having two or more layers, and preferably formed from a multilayer tube composed of three layers including an outer layer, an intermediate layer and an inner layer.

When the outer cylinder shaft 102 is composed of one-layer tube, the outer cylinder shaft 102 is preferably made of a polymeric material having an excellent antithrombogenicity since the outer cylinder shaft 102 comes into contact with biological tissue. Examples of the polymeric material include vinyl chloride, polyurethanes, polyamides, polyether block amide copolymers, polypropylene, polyolefins and polyethylene terephthalate. The polymeric material is preferably a polyurethane or a polyether block amide copolymer that matches the material of the balloon 101, to allow heat welding with the balloon.

When the outer cylinder shaft 102 is a multilayer tube, the outer layer of the outer cylinder shaft 102 is preferably made of a polymeric material having an excellent antithrombogenicity since the outer layer comes into contact with biological tissue. Examples of the polymeric material include vinyl chloride, polyurethanes, polyamides, polyether block amide copolymers, polypropylene, polyolefins and polyethylene terephthalate. The polymeric material is preferably a polyurethane or a polyether block amide copolymer that matches the material of the balloon 101, to allow heat welding with the balloon 101.

When the outer cylinder shaft 102 is a multilayer tube, the intermediate layer of the outer cylinder shaft 102 preferably includes, for example, flat wires made of a metal since durability and elasticity are required for the intermediate layer. For example, it is preferred to use stainless steel commonly used in medical devices, as the metal.

When the outer cylinder shaft 102 is a multilayer tube, the inner layer of the outer cylinder shaft 102 is preferably made of a polymeric material since slipperiness is required for the inner layer, and so that the tube as a whole has stretch resistance. It is preferred to use a fluorine-based polymer such as PTFE or a polyether block amide copolymer containing barium, as the polymeric material. From the viewpoint of adhesive property, it is preferred to use a polyether block amide copolymer containing barium.

In the formation of the above-described multilayer tube, the materials to be used for satisfying the properties required for the outer layer, the inner layer and the tube as a whole are not particularly limited, and the multilayer tube can be obtained using a method such as pasting using an adhesive, thermocompression bonding, multilayer formation by coextrusion, kneading and extrusion molding, resin impregnation or surface coating.

Inner Cylinder Shaft

Any tube-shaped member having flexibility can be used as the inner cylinder shaft 103, as well. For example, the inner cylinder shaft 103 is formed from a one-layer tube or a multilayer tube having two or more layers. From the viewpoint of preventing the buckling of the guide wire within the inner cylinder shaft 103, it is preferred to adjust the flexural rigidity depending on the application to be used, for example, by using a two-layer tube in which a hard material and a soft material are layered, as the inner cylinder shaft.

When the inner cylinder shaft 103 is a one-layer tube consisting of a layer of a polymeric material, examples of the polymeric material include polyamides, polyether block amides, polyimides, polyether ether ketones, polyphenylene sulfide, polyetherimides and polyamideimides, but not particularly limited thereto. A polyamide or a polyether block amide is preferred from the viewpoint of flexibility, and a polyether ether ketone is more preferred from the viewpoint of rigidity.

The inner cylinder shaft 103 preferably has a tensile elastic modulus of 500 to 1400 MPa, and a yield strength of 25 MPa or more, as the mechanical properties (test methods: ISO 527) thereof. Having a tensile elastic modulus of 500 MPa or more makes the inner cylinder shaft 103 less susceptible to deformation when the balloon 101 is stretched, and having a tensile elastic modulus of 1400 MPa or less facilitates the resulting catheter to pass through a curved portion such as the aortic arch. Having a yield strength of 25 MPa or more facilitates the resulting catheter to pass through a curved portion such as the aortic arch, as well. Further, the inner cylinder shaft 103 preferably has a wall thickness of 0.1 mm to 0.23 mm.

Figure 6:
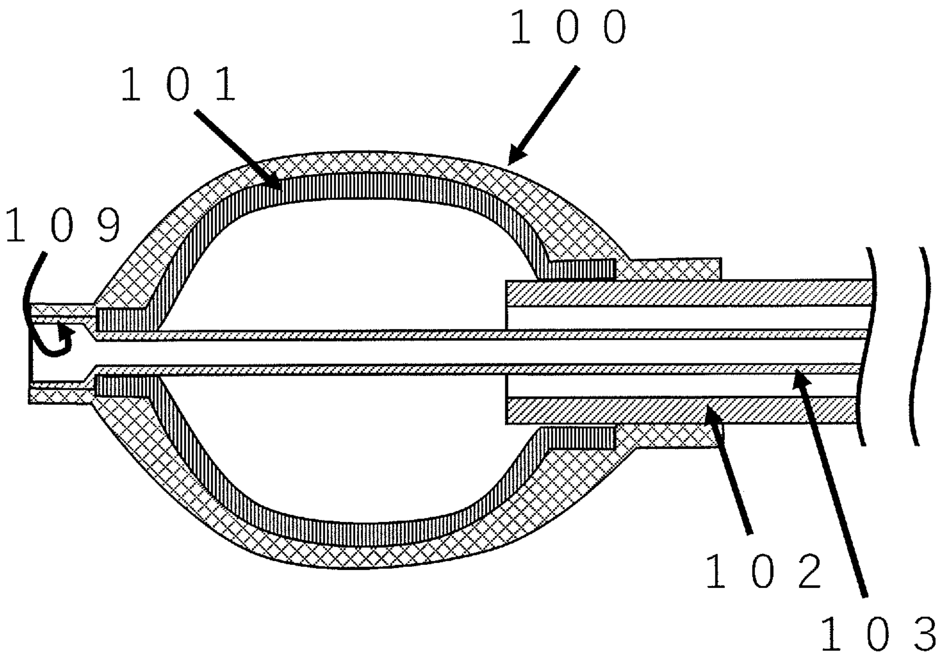
FIG. 6 is a cross-sectional view of a balloon catheter according to a third example, showing the vicinity of the balloon.

As in the balloon catheter according to the third example, shown in FIG. 6, the balloon catheter may be configured such that the inner cylinder shaft 103 includes: a large diameter portion 109 provided at the distal end of the inner cylinder shaft 103; a small diameter portion provided at the proximal end of the inner cylinder shaft 103 and having an inner diameter smaller than that of the large diameter portion 109; and a tapered portion connecting the large diameter portion and the small diameter portion; wherein the balloon 101 is fixed to the small diameter portion, and the securing member 100 is directly fixed to the large diameter portion. The balloon 101 is preferably fixed directly to the small diameter portion. When the length in the longitudinal direction of the portion to which the securing member 100 and the balloon 101 are fixed is increased due to directly fixing the securing member 100 onto the inner cylinder shaft 103, the inner diameter of the portion of the inner cylinder shaft 103 to which the securing member 100 is fixed is adjusted to that of the large diameter portion 109 to not impair the conformability to the guide wire when passing through a curved portion such as the aortic arch. This makes it possible to prevent the guide wire from being caught by the distal end portion of the inner cylinder shaft, even if the balloon catheter is in a curved state when passing through a curved portion. The dimensions of the large diameter portion 109 of the inner cylinder shaft are not particularly limited, as long as the conformability to a curved portion of the guide wire is not impaired. However, the inner diameter of the large diameter portion 109 of the inner cylinder shaft 103 is preferably 1.1 to 2 times the inner diameter of the small diameter portion of the inner cylinder shaft 103.

Distal End Member

Figure 7:
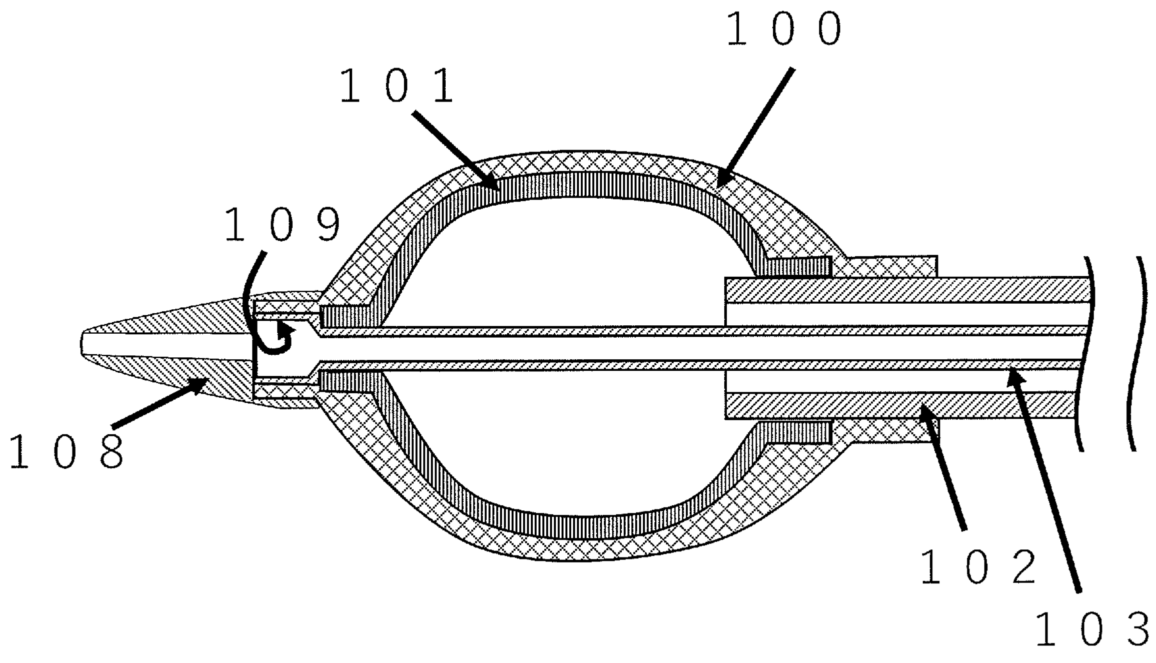
FIG. 7 is a cross-sectional view of a balloon catheter according to a fourth example, showing the vicinity of the balloon.

As in the balloon catheter according to the fourth example, shown in FIG. 7, the balloon catheter may further include a distal end member 108 having a tapered shape that narrows toward the distal end, at the distal end of the inner cylinder shaft 103. By including the distal end member 108 having a tapered shape that narrows toward the distal end, it is possible to decrease the clearance between the guide wire and the distal end of the inner cylinder shaft, to prevent the balloon catheter from being caught by a curved portion such as the aortic arch. When the inner cylinder shaft 103 includes a large diameter portion, the inner diameter of the distal end member 108 is preferably smaller than the inner diameter of the large diameter portion of the inner cylinder shaft 103. Further, the distal end member 108 is preferably made of a material having flexibility which does not impair the conformability to the guide wire, and which allows for diminishing the difference in hardness between the guide wire and the joined portion. Such a material is not particularly limited, but is preferably a polyether block amide copolymer containing barium sulfate, from the viewpoints of contrast properties and flexibility.

Adhesion of Securing Member, Balloon, Inner Cylinder Shaft and Outer Cylinder Shaft The adhesion of the respective members can be performed, for example, by a method such as adhesion using an adhesive, welding, welding (such as heat welding, vibration welding, ultrasonic welding or laser welding), insert injection molding, outsert injection molding or adhesion by winding a yarn, but not particularly limited thereto. For example, in a poorly weldable material such as natural rubber or a synthetic rubber, the adhesion may be performed by winding a yarn such as a fishing gut around each portion to be fixed. For use in an application requiring a high pressure, the securing member may be adhered by winding an aramid fiber therearound.

EXAMPLES

Example 1

A tube composed of three layers and having an outer diameter of 3.1 mm, an inner diameter of 2.6 mm and a length of 1050 m was formed, using a polyether block amide copolymer as the material of the outer layer, using stainless-steel flat wires as the material of the intermediate layer having a braided structure, and using a polyether block amide copolymer as the material of the inner layer.

Subsequently, a single-stepped pipe having a small diameter portion on the distal end side, and a large diameter portion on the proximal end side (which pipe is made of stainless steel, and in which pipe the small diameter portion has an outer diameter of 2 mm, an inner diameter of 1.84 mm and a length of 7 mm, and the large diameter portion has an outer diameter of 2.4 mm, an inner diameter of 2.24 mm and a length of 3 mm) was prepared. The end of an aramid fiber (having a length of 1200 mm and a diameter of 0.3 mm) was wound around and fixed to the step of the stepped pipe. After passing the aramid fiber through a braid tube, the large diameter portion of the stepped pipe and the distal end portion of the braid tube were fixed to each other with an adhesive (a cyanoacrylate-based adhesive, manufactured by Toagosei Co., Ltd.), to prepare the outer cylinder shaft 102.

A Y-shaped connector including a cap fitting portion to which an O-ring can be fitted was used as a holding member. The aramid fiber was arranged to extend in a tensioned state over the entire length of the lumen of the outer cylinder shaft 102, as a stretch prevention member. In a state where the aramid fiber was folded back onto the outer periphery of the end on the proximal end side of the outer cylinder shaft 102, the end on the proximal end side of the outer cylinder shaft 102 and the tube-connecting port of the Y-shaped connector were fixed to each other with an adhesive (a cyanoacrylate-based adhesive manufactured by ALTECO Co., Ltd.).

A stainless-steel pipe including a handle portion and having an outer diameter that varies in three steps was prepared as a push-in member. When the portions of the push-in member having different diameters are respectively defined as a large diameter portion, an intermediate portion and a small diameter portion, in the order from the proximal end side in the longitudinal direction, the large diameter portion had an outer diameter of 2.1 mm and a length of 60 mm, the intermediate portion had an outer diameter of 1.8 mm and a length of 10 mm, the taper length, which is the length of the portion shifting from the large diameter portion to the intermediate portion, was 0.5 mm, and the small diameter portion had an outer diameter of 1.16 mm and a length of 805 mm. The push-in member had a minimum inner diameter of 1.0 mm.

Subsequently, a screw-type cap for the holding member as well as an O-ring having an inner diameter of 1.4 mm and a wire diameter of 1.5 mm were inserted over the push-in member (such that the cap was located on the proximal end side). A pull-out prevention member was fixed with an adhesive (a cyanoacrylate-based adhesive, manufactured by Toagosei Co., Ltd.) to a position where the O-ring comes to the end on the proximal end side of the intermediate portion of the push-in member, onto the intermediate portion of the push-in member and on the side closer to the distal end than the O-ring. The pull-out prevention member was made of a polyimide, and had an inner diameter of 1.9 mm, a wall thickness of 0.06 mm and a length of 8.5 mm.

An inner layer tube (made of polyamide) having a tensile elastic modulus of 1300 MPa (test method: ISO 527) and a yield strength of 40 MPa (test method: ISO 527), and having an outer diameter of 1.2 mm, an inner diameter of 1.0 mm and a length of about 305 mm, was used as the tube that constitutes the inner cylinder shaft 103. The diameter of the end on the proximal end side of the tube was expanded, and the expanded end of the tube was fixed to the distal end portion of the small diameter portion of the push-in member with an adhesive (a cyanoacrylate-based adhesive, manufactured by Toagosei Co., Ltd.). Further, an outer layer tube (made of polyimide) having a flexural elastic modulus of 3.5 GPa (test method: ASTM D790) and a Rockwell hardness R of 126 (test method: ASTM D785), and having an inner diameter of 1.25 mm, an outer diameter of 1.37 mm and a length of 295 mm, was inserted over the inner layer tube that constitutes the inner cylinder shaft 103 such that the end on the proximal end side of the outer layer tube was in contact with the distal end of the small diameter portion of the pipe as the push-in member, and the portion of about 2 mm at the end on the proximal end side of the inner layer tube was fixed with the adhesive. The dimeter of the distal end of this inner layer tube was expanded, and a cylindrical stainless-steel pipe (having an outer diameter of 1.16 mm, an inner diameter of 1.0 mm and a length of 7 mm) was fitted to the lumen of the tube, and fixed with an adhesive (a cyanoacrylate-based adhesive, manufactured by Toagosei Co., Ltd.). Further, the distal end of the outer layer tube and the distal end of the inner layer tube were fixed to each other with the adhesive. The resultant was taken as the inner cylinder shaft 103. An inner cylinder shaft assembly composed of the inner cylinder shaft 103 and the push-in member was inserted into an outer cylinder shaft assembly, and the cap for the holding member was fitted to the holding member.

Natural rubber having an inner diameter of 4.5 mm and a film thickness on one side of 0.3 mm was fixed onto the small diameter portion of the stepped pipe of the outer cylinder shaft 102 and onto the stainless-steel pipe of the inner cylinder shaft 103, by winding a #0.6 Nylon fishing gut having a length of 3 mm around each fixing portion and adhering with an adhesive (a cyanoacrylate-based adhesive, manufactured by Toagosei Co., Ltd.), to obtain a balloon. In this manner, the balloon 101 composed of one layer of natural rubber and having a round shape was obtained. At this time, the balloon was formed to have an equilibrium length of 25 mm.

Forty-eight sets of round wire bundles each composed of three wires and made of SUS 304 (Young's modulus: 140 MPa, tensile strength; 2300 MPa) were prepared as the material of the securing member 100. The wire bundles were oriented at an angle to be symmetrical with each other with respect to the axis, and crossed to form a braided structure, to be used as the securing member 100. The round wires forming the securing member each had a cross-sectional area of 0.0019 mm$^2$. The resulting securing member 100 was disposed on the outer periphery of the balloon 101, and the operation of winding a liquid crystal polyester yarn with a fineness of 425 dtex around the rear end portion of the securing member 100 to cover the portion at which the balloon 101 had been fixed to the distal end portion of the outer cylinder shaft 102 by winding the Nylon fishing gut therearound, and of fixing the wound portion with an adhesive (a cyanoacrylate-based adhesive, manufactured by Toagosei Co., Ltd.), was repeated three times. Further, the operation of winding a liquid crystal polyester yarn with a fineness of 425 dtex around the distal end portion of the securing member 100 to cover the portion at which the balloon 101 had been fixed to the distal end portion of the inner cylinder shaft 103 by winding the Nylon fishing gut therearound, and of fixing the wound portion with an adhesive (a cyanoacrylate-based adhesive, manufactured by Toagosei Co., Ltd.), was repeated three times. In this manner, the distal end portion of the inner cylinder shaft 103 and the rear end portion of the securing member 100 were fixed to each other, and the distal end portion of the outer cylinder shaft 102 and the rear end portion of the securing member 100 were fixed to each other with the balloon interposed therebetween, thereby completing the balloon catheter 10.

Example 2

A balloon catheter was produced in the same manner as in Example 1, except that the material of the securing member 100 was changed to SUS 304 having a cross-sectional area of 0.0038 mm$^2$.

Example 3

A balloon catheter was produced in the same manner as in Example 1, except that the balloon 101 was changed to a balloon composed of two layers, obtained by: using as the inner layer, a layer of natural rubber having an inner diameter of 4.5 mm and a film thickness on one side of 0.3 mm, and using as the surface layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m; and adhering the layers with a rubber cement (KST-1; manufactured by SOGOU SYOUTEN Co., Ltd.).

Example 4

A balloon catheter was produced in the same manner as in Example 1, except that the material of the securing member 100 was changed to SUS 304 having a cross-sectional area of 0.0038 mm$^2$, and that the balloon 101 was changed to a balloon composed of two layers, obtained by: using as the inner layer, a layer of natural rubber having an inner diameter of 4.5 mm and a film thickness on one side of 0.3 mm, and using as the surface layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m; and adhering the layers with a rubber cement (KST-1; manufactured by SOGOU SYOUTEN Co., Ltd.).

Example 5

A balloon catheter was produced in the same manner as in Example 1, except that the material of the securing member 100 was changed to SUS 304 having a cross-sectional area of 0.0038 mm$^2$, and that the balloon 101 was changed to a balloon composed of three layers, obtained by: using as the inner layer, a layer of natural rubber having an inner diameter of 4.5 mm and a film thickness on one side of 0.3 mm, using as the intermediate layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m, and using as the surface layer, a layer of natural rubber having an inner diameter of 4.5 mm and a film thickness on one side of 0.3 mm; and adhering the respective layers with a rubber cement (KST-1; manufactured by SOGOU SYOUTEN Co., Ltd.).

Example 6

A balloon catheter was produced in the same manner as in Example 1, except that the material of the securing member 100 was changed to SUS 304 having a cross-sectional area of 0.0063 mm$^2$, and that the balloon 101 was changed to a balloon composed of three layers, obtained by: using as the inner layer, a layer of natural rubber having an inner diameter of 4.5 mm and a film thickness on one side of 0.3 mm, using as the intermediate layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m, and using as the surface layer, a layer of natural rubber having an inner diameter of 4.5 mm and a film thickness on one side of 0.3 mm; and adhering the respective layers with a rubber cement (KST-1; manufactured by SOGOU SYOUTEN Co., Ltd.).

Example 7

A balloon catheter was produced in the same manner as in Example 1, except that the material of the securing member

100 was changed to SUS 304 having a cross-sectional area of 0.0095 $mm^2$, and that the balloon 101 was changed to a balloon composed of three layers, obtained by: using as the inner layer, a layer of natural rubber having an inner diameter of 4.5 mm and a film thickness on one side of 0.3 mm, using as the intermediate layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m, and using as the surface layer, a layer of natural rubber having an inner diameter of 4.5 mm and a film thickness on one side of 0.3 mm; and adhering the respective layers with a rubber cement (KST-1; manufactured by SOGOU SYOUTEN Co., Ltd.).

Example 8

A balloon catheter was produced in the same manner as in Example 1, except that the material of the securing member 100 was changed to tungsten (Young's modulus: 270 GPa, tensile strength: 2800 MPa) having a cross-sectional area of 0.0063 $mm^2$, and that the balloon 101 was changed to a balloon composed of three layers, obtained by: using as the inner layer, a layer of natural rubber having an inner diameter of 4.5 mm and a film thickness on one side of 0.3 mm, using as the intermediate layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m, and using as the surface layer, a layer of natural rubber having an inner diameter of 4.5 mm and a film thickness on one side of 0.3 mm; and adhering the respective layers with a rubber cement (KST-1; manufactured by SOGOU SYOUTEN Co., Ltd.).

Example 9

A balloon catheter was produced in the same manner as in Example 1, except for the following changes. The stainless-steel pipe attached to the distal end of the inner cylinder shaft 103 was changed to a stainless-steel single-stepped pipe (in which the small diameter portion has an outer diameter of 1.16 mm, an inner diameter of 1.00 mm and a length of 5 mm, and the large diameter portion has an outer diameter of 1.7 mm, an inner diameter of 1.5 mm and a length of 6 mm). Further, the distal end portion of the securing member 100 was directly fixed to the large diameter portion at the distal end of the inner cylinder shaft 103, and the distal end portion of the balloon 101 was directly fixed to the distal end side of the small diameter portion of the inner cylinder shaft 103.

Thereafter, the distal end member 108 was fitted to the distal end portion of the inner cylinder shaft 103 to which the securing member 100 had been attached, and fixed with an adhesive (a cyanoacrylate-based adhesive, manufactured by Toagosei Co., Ltd.), to prepare the balloon catheter of Example 9. When the portions of the distal end member 108 having different diameters were respectively defined as a large diameter portion and a small diameter portion, from the proximal end side in the longitudinal direction, the large diameter portion had an outer diameter of 4.1 mm, an inner diameter of 3.9 mm and a length of 5 mm, and the small diameter portion, which had a tapered shape shifting from the large diameter portion to the small diameter portion and having a tapering length of 8 mm, had a minimum outer diameter of 1.34 mm and an inner diameter of 0.94 mm. The distal end member was made of a polyether block amide copolymer.

Example 10

A balloon catheter was produced in the same manner as in Example 1, except for the following changes. The material of the securing member 100 was changed to SUS 304 having a cross-sectional area of 0.0095 $mm^2$. In addition, the balloon 101 was changed to a balloon composed of three layers, obtained by using as the inner layer, a layer of polyurethane having a maximum outer diameter of 14 mm and a film thickness on one side of 0.04 mm, using as the intermediate layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m, and using as the surface layer, a layer of polyurethane having a maximum outer diameter of 16 mm and a film thickness on one side of 0.04 mm, which balloon had been fixed by winding a #0.6 Nylon fishing gut having a length of 3 mm around each fixing portion, and adhering with an adhesive (a cyanoacrylate-based adhesive, manufactured by Toagosei Co., Ltd.).

Example 11

A balloon catheter was produced in the same manner as in Example 1, except for the following changes. The material of the securing member 100 was changed to nickel-titanium (Young's modulus: 64 GPa, tensile strength: 2100 MPa) having a cross-sectional area of 0.0123 $mm^2$. In addition, the balloon 101 was changed to a balloon composed of three layers, obtained by using as the inner layer, a layer of polyurethane having a maximum outer diameter of 14 mm and a film thickness on one side of 0.04 mm, using as the intermediate layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m, and using as the surface layer, a layer of polyurethane having a maximum outer diameter of 16 mm and a film thickness on one side of 0.04 mm, which balloon had been fixed by winding a #0.6 Nylon fishing gut having a length of 3 mm around each fixing portion, and adhering with an adhesive (a cyanoacrylate-based adhesive, manufactured by Toagosei Co., Ltd.).

Example 12

A balloon catheter was produced in the same manner as in Example 1, except for the following changes. The material of the securing member 100 was changed to SUS 304 having a cross-sectional area of 0.0095 $mm^2$. In addition, the balloon 101 was changed to a balloon composed of three layers, obtained by: using as the inner layer, a layer of natural rubber having an inner diameter of 4.5 mm and a film thickness on one side of 0.3 mm, using as the intermediate layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m, and using as the surface layer, a layer of natural rubber having an inner diameter of 4.5 mm and a film thickness on one side of 0.3 mm; and adhering the respective layers with a rubber cement (KST-1; manufactured by SOGOU SYOUTEN Co., Ltd.). Moreover, the operation of winding a double twisted yarn of para-aramid fibers each having a fineness of 1100 dtex around the rear end portion of the securing member 100, winding a double twisted yarn of para-aramid fibers each having a fineness of 1100 dtex around the distal end portion of the securing member 100, and fixing the wound portions with an adhesive, was performed once.

Comparative Example 1

A balloon catheter was produced in the same manner as in Example 1, except that the securing member 100 was not used.

Comparative Example 2

A balloon catheter was produced in the same manner as in Example 1, except that the securing member 100 was not used, and that the balloon 101 was changed to a balloon composed of two layers, obtained by: using as the inner layer, a layer of natural rubber having an inner diameter of 4.5 mm and a film thickness on one side of 0.3 mm, and using as the surface layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m; and adhering the layers with a rubber cement (KST-1; manufactured by SOGOU SYOUTEN Co., Ltd.).

Comparative Example 3

A balloon catheter was produced in the same manner as in Example 1, except that the securing member 100 was not used, and that the balloon 101 was changed to a balloon composed of three layers, obtained by: using as the inner layer, a layer of natural rubber having an inner diameter of 4.5 mm and a film thickness on one side of 0.3 mm, using as the intermediate layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m, and using as the surface layer, a layer of natural rubber having an inner diameter of 4.5 mm and a film thickness on one side of 0.3 mm; and adhering the respective layers with a rubber cement (KST-1; manufactured by SOGOU SYOUTEN Co., Ltd.).

Comparative Example 4

A balloon catheter was produced in the same manner as in Example 1, except for the following changes. The material of the securing member 100 was changed to SUS 304 having a cross-sectional area of 0.0095 $mm^2$. Further, the balloon 101 was changed to a balloon having a three layer structure, obtained by: using as the inner layer, a layer of natural rubber having an inner diameter of 4.5 mm and a film thickness on one side of 0.3 mm, using as the intermediate layer, a mesh knitted in the form of a cylinder with the number of stitches of 50, using false twisted yarns formed by Z-twisting polyurethane fibers (33 dtex) and polyester fibers (78 dtex) with the number of false twists of 424 t/m, and using as the surface layer, a layer of natural rubber having an inner diameter of 4.5 mm and a film thickness on one side of 0.3 mm; and adhering the respective layers with a rubber cement (KST-1; manufactured by SOGOU SYOUTEN Co., Ltd.). In addition, the securing member 100 were adhered to the balloon 101 with an adhesive (a cyanoacrylate-based adhesive, manufactured by Toagosci Co., Ltd.).

The differences in structure between the balloon catheters of Examples 1 to 9 are summarized in Table 1, and the differences in structure between the balloon catheters of Comparative Examples 1 to 4 are summarized in Table 2.

TABLE 1

| | Item | Example 1 | Example 2 | Example 3 | Example 4 | Example 5 | Example 6 | Example 7 |
|---|---|---|---|---|---|---|---|---|
| Securing member | Material | SUS304 | SUS304 | SUS304 | SUS304 | SUS304 | SUS304 | SUS304 |
| | Young's modulus (GPa) | 140 | 140 | 140 | 140 | 140 | 140 | 140 |
| | Tensile strength (MPa) | 2300 | 2300 | 2300 | 2300 | 2300 | 2300 | 2300 |
| | Cross-sectional area ($mm^2$) | 0.0019 | 0.0038 | 0.0019 | 0.0019 | 0.0038 | 0.0063 | 0.0095 |
| Material of balloon | Inner layer | Natural rubber | Natural rubber | Natural rubber | Natural rubber | Natural rubber | Natural rubber | Natural rubber |
| | Intermediate layer | — | — | — | — | Braided layer | Braided layer | Braided layer |
| | Surface layer | — | — | Braided layer | Braided layer | Natural rubber | Natural rubber | Natural rubber |
| Inner cylinder shaft | Distal end shape | Cylinder | Cylinder | Cylinder | Cylinder | Cylinder | Cylinder | Cylinder |

| | Item | Example 8 | Example 9 | Example 10 | Example 11 | Example 12 |
|---|---|---|---|---|---|---|
| Securing member | Material | Tungsten | SUS304 | SUS304 | Nickel-titanium | SUS304 |
| | Young's modulus (GPa) | 270 | 140 | 140 | 64 | 140 |
| | Tensile strength (MPa) | 2800 | 2300 | 2300 | 2100 | 2300 |
| | Cross-sectional area ($mm^2$) | 0.0063 | 0.0019 | 0.0095 | 0.0123 | 0.0095 |

TABLE 1-continued

| | | | | | | |
|---|---|---|---|---|---|---|
| Material of balloon | Inner layer | Natural rubber | Natural rubber | Poly-urethane | Poly-urethane | Natural rubber |
| | Intermediate layer | Braided layer | — | Braided layer | Braided layer | Braided layer |
| | Surface layer | Natural rubber | — | Poly-urethane | Poly-urethane | Natural rubber |
| Inner cylinder shaft | Distal end shape | Cylinder | Single-stepped shape | Cylinder | Cylinder | Round |

TABLE 2

| | Item | Comparative Example 1 | Comparative Example 2 | Comparative Example 3 | Comparative Example 4 |
|---|---|---|---|---|---|
| Securing member | Material | — | — | — | SUS304 |
| | Young's modulus (GPa) | — | — | — | 140 |
| | Tensile strength (MPa) | — | — | — | 2300 |
| | Cross-sectional area (mm$^2$) | — | — | — | 0.0095 |
| Material of balloon | Inner layer | Natural rubber | Natural rubber | Natural rubber | Natural rubber (Reinforcing member and surface layer of elastic balloon are adhered with each other) |
| | Intermediate layer | — | — | Braided layer | Braided layer |
| | Surface layer | — | Braided layer | Natural rubber | Natural rubber |
| Inner cylinder | Distal end shape | Cylinder | Cylinder | Cylinder | Cylinder |

The properties of the balloon catheters of Examples 1 to 8 and Comparative Examples 1 to 4 were measured by performing the following tests: (1) Test of capacity to pass external fluid and inflated position retainment, and (2) Pressure resistance test, in the order mentioned, and the results thereof are summarized in Tables 3 and 4. Further, the property of the balloon catheter of Example 9 was measured by performing the following test: (3) Test of conformability to simulated blood vessel loop, and the result thereof is summarized in Table 5.

(1) Test of Capacity to Pass External Fluid and Inflated Position Retainment

A mark was made on the central portion of a transparent hose (inner diameter: 18 mm, length: 1000 mm) with a black permanent marker, and then a guide wire (medical device approval number: 22400BZX00511000; manufactured by Cook Medical Technologies LLC) having a diameter of 0.035 inches and a length of 260 cm was placed to pass through the interior of the hose. Thereafter, the balloon was inserted into the hose along the guide wire, and placed such that the central position of the balloon overlapped with the mark made on the hose. Water colored with a dye (edible pigment, red; manufactured by Kyoritsu Foods Co., Ltd.) adjusted to a temperature of 36° C., as the external fluid, was introduced into the hose at a flow rate of 5 L/min, using a liquid transfer pump. The term "inflated position" refers to a desired position for treating a stenosis or the like by inflating the balloon. In the present test, however, the "inflated position" is defined as the position of the mark made on the transparent hose.

A. Confirmation Method in Example of Balloon Catheter Including Securing Member

The holding portion of the balloon catheter was pulled to expand the diameter of the securing member alone. At this time, whether or not the external fluid can pass over the balloon was confirmed by observing the transparent hose from the exterior thereof, and by visually observing the change in the flow rate of the fluid flowing out of the hose. Thereafter, the balloon was inflated while keeping the water running, and whether or not the central position of the balloon shifted from the mark made on the hose was visually observed.

B. Confirmation Method in Example of Balloon Catheter Not Including Securing Member Whether or not the external fluid can pass over the balloon when the balloon is inflated was confirmed by observing the transparent hose from the exterior thereof, and by visually observing the change in the flow rate of the fluid flowing out of the hose. Further, whether or not the central position of the balloon shifted from the mark made on the hose, before and after the inflation, was visually observed.

The results of the change in the flow rate of the external fluid and the shift in the central position of the balloon, depending on the presence or absence of the securing member, as observed by the methods A and B, were evaluated as ○, Δ or x, in accordance with the following evaluation criteria.

○: The flow of the external fluid did not stop, and the position of the balloon did not shift before and after the inflation of the balloon.

Δ: The flow of the external fluid did not stop, but the position of the balloon shifted before and after the inflation of the balloon.

Δ: The flow of the external fluid stopped, but the position of the balloon did not shift before and after the inflation of the balloon.

x: The flow of the external fluid stopped, and the position of the balloon shifted before and after the inflation of the balloon.

(2) Pressure Resistance Test

An annular-shaped object having a thickness of 5 mm, a width of 10 mm and an inner diameter of 19 mm was formed by a 3D printer (AGILISTA-3200; manufactured by KEYENCE CORPORATION), using an acrylic resin (AR-M2; manufactured by KEYENCE CORPORATION) as the material, and the thus formed object was used as a simulated valve. An indeflator (registration number: 13B1X10229MM0005; manufactured by Merit Medical Systems, Inc.) and a pressure sensor (AP-V80; manufactured by KEYENCE CORPORATION) were connected to the catheter.

A. Method of Confirming Maximum Inflation Pressure in Example of Balloon Catheter Including Securing Member The balloon was inserted into the inner side of the simulated valve, and the holding portion of the balloon catheter was pulled to expand the diameter of the securing member so that the securing member came into contact with the inner wall of the frame of the prosthetic valve. Thereafter, the handle of the indeflator was turned to inject water as the internal fluid into the shaft, thereby inflating the balloon. The value of the pressure sensor when the balloon fractured was recorded as the maximum inflation pressure.

such that the pressure-resistant hose was not flattened. The resultant was used as a simulated blood vessel. The curvature of the thus prepared loop had a diameter of 5 cm, when the central axis in the cross section of the pressure-resistant hose was taken as the circumference of the loop. The end portion of the pressure-resistant hose on the side at which the loop was formed constitutes the distal end side of the simulated blood vessel.

A guide wire (medical device approval number: 22400BZX00511000; manufactured by Cook Medical Technologies LLC) having a diameter of 0.035 inches and a length of 260 cm was placed to pass through the interior of the simulated blood vessel and the introducer sheath. Thereafter, the balloon catheter of each of the Examples and Comparative Examples was inserted into the interior of the simulated blood vessel along the guide wire from the proximal end side, to evaluate whether or not the balloon catheter can be inserted conforming to the guide wire. The conformability to the loop in the simulated blood vessel was evaluated in accordance with the following evaluation criteria.

○: The balloon catheter was successfully inserted without any problem as described in "x" below (namely, has a good conformability).

x: A problem that the balloon catheter fails to conform to the guide wire when inserted into the loop in the simulated blood vessel, to cause the occurrence of deformation in the shape of the guide wire, or that the balloon catheter causes the peeling of the coating of the guide wire, was observed (namely, has a poor conformability).

TABLE 3

| Item | Example 1 | Example 2 | Example 3 | Example 4 | Example 5 | Example 6 | Example 7 | Example 8 | Example 10 | Example 11 | Example 12 |
|---|---|---|---|---|---|---|---|---|---|---|---|
| Test of Capacity to Pass External Fluid | ○ | ○ | ○ | ○ | ○ | ○ | ○ | ○ | ○ | ○ | ○ |
| Test of Inflated Position Retainment | ○ | ○ | ○ | ○ | ○ | ○ | ○ | ○ | ○ | ○ | ○ |
| Pressure Resistance Test | ○ | ○ | ○ | ○ | ○ | ○ | ○ | ○ | ○ | ○ | ○ |
| Value of maximum inflation pressure | 3 atm | 5 atm | 5 atm | 7 atm | 10 atm | 20 atm | 30 atm | 30 atm | 30 atm | 30 atm | 30 atm |

B. Method of Confirming Maximum Inflation Pressure in Example of Balloon Catheter Not Including Securing Member The balloon was inserted into the inner side of the simulated valve, and the handle of the indeflator was turned to inject water as the internal fluid into the shaft, thereby inflating the balloon. The value of the pressure sensor when the balloon fractured was recorded as the maximum inflation pressure.

The impact of the presence or absence of the securing member on the maximum inflation pressure, as observed by the methods A and B, were evaluated as ○ or x, in accordance with the following evaluation criteria.

○: The maximum inflation pressure is higher as compared to the example of not including the securing member.

x: The maximum inflation pressure is lower as compared to the example of not including the securing member.

(3) Test of Conformability to Simulated Blood Vessel Loop

Using a transparent pressure-resistant hose (inner diameter: 25 mm, length: 70 cm), one round of loop was formed such that the center of the loop was located at a position of about 16 cm from the end of the pressure-resistant hose, and

TABLE 4

| Item | Comparative Example 1 | Comparative Example 2 | Comparative Example 3 | Comparative Example 4 |
|---|---|---|---|---|
| Test of Capacity to Pass External Fluid | X | X | X | X |
| Test of Inflated Position Retainment | X | X | X | X |
| Pressure Resistance Test | X | X | X | ○ |
| Value of maximum inflation pressure | 1 atm | 4 atm | 5 atm | 30 atm |

TABLE 5

| Item | Example 9 |
|---|---|
| Test of conformability to simulated blood vessel loop | ○ |

In the test of capacity to pass external fluid and inflated position retainment, as shown in Tables 3 and 4, the passing of the water was confirmed in the balloon catheters of Examples 1 to 8 and 10 to 12, and each balloon catheter was successfully fixed without shifting from the desired position. In the balloon catheters of Comparative Examples 1 to 4, in contrast, the passing of the water was not confirmed, and each balloon catheter shifted from the desired position when the balloon was inflated.

In the pressure resistance test, as shown in Tables 3 and 4, the balloon catheters of Examples 1 and 2, each including a balloon consisting of one layer of natural rubber and including the securing member, showed a higher inflation pressure until the fracture of the balloon as compared to the balloon catheter of Comparative Example 1 which does not include the securing member, regardless of using a balloon having the same structure, and achieved a pressure resistance of 3 atm or more. The balloon catheters of Examples 3 and 4, each including a balloon composed of two layers in which natural rubber was used for the inner layer and the braided layer of resin fibers was used for the surface layer, and including the securing member, showed a higher inflation pressure until the fracture of the balloon as compared to the balloon catheter of Comparative Example 2 which does not include the securing member, and achieved a pressure resistance of 7 atm or more. Further, the balloon catheters of Examples 5 to 8 and 12, each including a balloon composed of three layers in which natural rubber was used for the surface layer, the braided layer was used for the intermediate layer and natural rubber was used for the inner layer, and including the securing member, as well as the balloon catheters of Examples 10 and 11, each including a balloon composed of three layers in which polyurethane is used for the surface layer, the braided layer was used for the intermediate layer and polyurethane was used for the inner layer, and including the securing member, showed a higher inflation pressure until the fracture of the balloon as compared to the balloon catheter of Comparative Example 3 which does not include the securing member, and achieved a pressure resistance of 20 atm or more. As described above, an improvement in the pressure resistance was observed, by providing the securing member on the outer peripheral side of the balloon, and expanding the diameter of the securing member before the inflation of the balloon.

In the balloon catheter of Comparative Example 4, although the pressure resistance is improved as compared to the balloon catheter of Comparative Example 3 which does not include the securing member, the occurrence of the blocking of the blood flow and a shift in the inflated position were confirmed, because the securing member and the balloon were joined at their surfaces. This confirmed that providing the securing member on the exterior of the balloon improves the pressure resistance, but it results in a failure to allow the external fluid to pass and a failure to retain the inflated position.

Based on the values of the maximum inflation pressure confirmed in the pressure resistance test shown in Tables 3 and 4, we believe that an inflation pressure of 2 to 3 atm, which is required for treating aortic valve stenosis, as described above, can be achieved when the wires forming the securing member have a cross-sectional area of 0.0019 $mm^2$ or more, and the balloon has a structure of one or more layers of an elastic material. Further, we believe that an inflation pressure of 7 atm or more, which is required for placing a stent, as described above, can be achieved when the wires forming the securing member have a cross-sectional area of 0.0038 $mm^2$ or more, and the balloon has a structure of two or more layers including a layer of an elastic material and a braided layer. Still further, we believe that an inflation pressure of 15 atm or more, which is required for fracturing prosthetic valve, as described above, can be achieved when the wires forming the securing member have a cross-sectional area of 0.0063 $mm^2$ or more, and the balloon has a structure of three or more layers including a layer of an elastic material and a braided layer.

The test of conformability to simulated blood vessel loop is a simulated reproduction of the operation of delivering the balloon catheter to an affected area, carried out to investigate whether or not the balloon catheter can be inserted conforming to the guide wire present in a curved portion of a blood vessel. As shown in Table 5, the balloon catheter of Example 9 was evaluated as having a good conformability.

INDUSTRIAL APPLICABILITY

We enable performance of a wide range of techniques, ranging from a technique that requires a high pressure resistance such as fracturing prosthetic valve, which has conventionally been difficult, to aortic valve inflation which can be performed even with a low pressure resistance.

The invention claimed is:

1. A balloon catheter comprising:

an outer cylinder shaft having flexibility;

an inner cylinder shaft having flexibility and within said outer cylinder shaft;

a balloon fixed to said outer cylinder shaft, that inflates or deflates in a transverse direction due to a pressure of an internal fluid supplied through a space within said outer cylinder shaft; and a securing member provided on an outer peripheral side of said balloon, whose diameter expands or contracts in the transverse direction independently of said balloon, due to a mutual movement of said outer cylinder shaft and said inner cylinder shaft in a longitudinal direction thereof;

wherein a distal end portion of said inner cylinder shaft and a distal end portion of said securing member are fixed to each other, and a distal end portion of said outer cylinder shaft and a proximal end portion of said securing member are fixed to each other; and said securing member has an opening(s) through which an external fluid can pass when the diameter of said securing member is expanded.

2. The balloon catheter according to claim 1, wherein said securing member is composed of a wire(s), and said wire(s) has/have any one of a braided form, a woven form, a helical form and a linear form.

3. The balloon catheter according to claim 2, wherein said wire has a Young's modulus of 60 to 500 GPa, and a tensile strength of 500 MPa or more.

4. The balloon catheter according to claim 3, wherein said inner cylinder shaft comprises:

a large diameter portion provided at a distal end of said inner cylinder shaft; and a small diameter portion provided at a proximal end of said inner cylinder shaft, and having an inner diameter smaller than that of said large diameter portion;

said balloon is fixed to said small diameter portion of said inner cylinder shaft; and said securing member is directly fixed to said large diameter portion of said inner cylinder shaft.

5. The balloon catheter according to claim 3, wherein said wire has a cross-sectional area of 0.0019 $mm^2$ or more;

said balloon is composed of one or more layers including a layer of an elastic material; and said balloon catheter is configured to be used for the treatment of aortic valve stenosis.

6. The balloon catheter according to claim 3, wherein said wire has a cross-sectional area of 0.0038 $mm^2$ or more;

said balloon is composed of two or more layers including a layer of an elastic material and a braided layer of resin fibers; and said balloon catheter is configured to be used for inflating a stent.

7. The balloon catheter according to claim 3, wherein said wire has a cross-sectional area of 0.0063 $mm^2$ or more;

said balloon is composed of three or more layers including a layer of an elastic material and a braided layer of resin fibers; and said balloon catheter is configured to be used for fracturing a prosthetic valve.

8. The balloon catheter according to claim 2, wherein said wire has a cross-sectional area of 0.0019 $mm^2$ or more;

said balloon is composed of one or more layers including a layer of an elastic material; and said balloon catheter is configured to be used for the treatment of aortic valve stenosis.

9. The balloon catheter according to claim 2, wherein said wire has a cross-sectional area of 0.0038 $mm^2$ or more;

said balloon is composed of two or more layers including a layer of an elastic material and a braided layer of resin fibers; and said balloon catheter is configured to be used for inflating a stent.

10. The balloon catheter according to claim 2, wherein said wire has a cross-sectional area of 0.0063 $mm^2$ or more;

said balloon is composed of three or more layers including a layer of an elastic material and a braided layer of resin fibers; and said balloon catheter is configured to be used for fracturing a prosthetic valve.

11. The balloon catheter according to claim 2, wherein said wire has a Young's modulus of 60 to 500 GPa, and a tensile strength of 500 MPa or more.

12. The balloon catheter according to claim 2, wherein said inner cylinder shaft comprises:

a large diameter portion provided at a distal end of said inner cylinder shaft; and a small diameter portion provided at a proximal end of said inner cylinder shaft, and having an inner diameter smaller than that of said large diameter portion;

said balloon is fixed to said small diameter portion of said inner cylinder shaft; and said securing member is directly fixed to said large diameter portion of said inner cylinder shaft.

13. The balloon catheter according to claim 2, wherein said wire has a cross-sectional area of 0.0019 $mm^2$ or more;

said balloon is composed of one or more layers including a layer of an elastic material; and said balloon catheter is configured to be used for the treatment of aortic valve stenosis.

14. The balloon catheter according to claim 2, wherein said wire has a cross-sectional area of 0.0019 $mm^2$ or more;

said balloon is composed of one or more layers including a layer of an elastic material; and said balloon catheter is configured to be used for the treatment of aortic valve stenosis.

15. The balloon catheter according to claim 2, wherein said wire has a cross-sectional area of 0.0038 $mm^2$ or more;

said balloon is composed of two or more layers including a layer of an elastic material and a braided layer of resin fibers; and said balloon catheter is configured to be used for inflating a stent.

16. The balloon catheter according to claim 2, wherein said wire has a cross-sectional area of 0.0038 $mm^2$ or more;

said balloon is composed of two or more layers including a layer of an elastic material and a braided layer of resin fibers; and said balloon catheter is configured to be used for inflating a stent.

17. The balloon catheter according to claim 2, wherein said wire has a cross-sectional area of 0.0063 $mm^2$ or more;

said balloon is composed of three or more layers including a layer of an elastic material and a braided layer of resin fibers; and said balloon catheter is configured to be used for fracturing a prosthetic valve.

18. The balloon catheter according to claim 2, wherein said wire has a cross-sectional area of 0.0063 $mm^2$ or more;

said balloon is composed of three or more layers including a layer of an elastic material and a braided layer of resin fibers; and said balloon catheter is configured to be used for fracturing a prosthetic valve.

19. The balloon catheter according to claim 1, wherein said inner cylinder shaft comprises:

a large diameter portion provided at a distal end of said inner cylinder shaft; and a small diameter portion provided at a proximal end of said inner cylinder shaft, and having an inner diameter smaller than that of said large diameter portion;

said balloon is fixed to said small diameter portion of said inner cylinder shaft; and said securing member is directly fixed to said large diameter portion of said inner cylinder shaft.

* * * * *